US 11,173,253 B2

(12) United States Patent
Sanders et al.

(10) Patent No.: US 11,173,253 B2
(45) Date of Patent: Nov. 16, 2021

(54) PACKAGING FOR SAFETY NEEDLE

(71) Applicant: Becton, Dickinson and Company, Franklin Lakes, NJ (US)

(72) Inventors: Laurie Sanders, Glen Ridge, NJ (US); Edward P. Browka, Sherrill, NY (US); Peter Smith, Cary, NC (US); Adam Kristopher Brakoniecki, New York, NY (US); Alice Wong, Leonia, NJ (US); Regina Haywood, Franklin Lakes, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 16/810,476

(22) Filed: Mar. 5, 2020

(65) Prior Publication Data
US 2020/0282149 A1    Sep. 10, 2020

Related U.S. Application Data

(63) Continuation-in-part of application No. 15/837,018, filed on Dec. 11, 2017, now abandoned.

(60) Provisional application No. 62/433,044, filed on Dec. 12, 2016, provisional application No. 62/479,507, filed on Mar. 31, 2017, provisional application No. 62/479,563, filed on Mar. 31, 2017.

(51) Int. Cl.
*B65D 75/36* (2006.01)
*A61M 5/32* (2006.01)
*A61M 5/00* (2006.01)
*B65D 75/32* (2006.01)

(52) U.S. Cl.
CPC .......... *A61M 5/3202* (2013.01); *A61M 5/002* (2013.01); *B65D 75/327* (2013.01); *B65D 75/36* (2013.01); *B65D 2575/3227* (2013.01)

(58) Field of Classification Search
CPC ... A61M 5/3202; A61M 5/002; B65D 75/327; B65D 75/36; B65D 2575/3227
USPC .................................................. 206/364, 370
See application file for complete search history.

(56) References Cited

U.S. PATENT DOCUMENTS

| 2,023,289 A | 12/1935 | Pringle |
| 2,557,222 A | 6/1951 | Goode |
| 3,367,488 A | 2/1968 | Hamilton |

(Continued)

FOREIGN PATENT DOCUMENTS

| CA | 2551835 A1 | 8/2005 |
| CA | 2803761 A1 | 12/2011 |

(Continued)

OTHER PUBLICATIONS

Final Office Action in U.S. Appl. No. 15/837,012 dated Feb. 10, 2020, 25 pages.

(Continued)

*Primary Examiner* — Jacob K Ackun
(74) *Attorney, Agent, or Firm* — Servilla Whitney LLC

(57) ABSTRACT

Single and dual packaging for fill needles and safety needles are described herein. Such packaging can include hard packaging or blister packs. Such packaging can include a premature activation prevention element disposed on an inner sidewall of a compartment of the packaging to nest within a recess of a tether of a safety needle device to prevent accidental activation of the safety needle device prior to use by the user.

20 Claims, 13 Drawing Sheets

(56) References Cited

U.S. PATENT DOCUMENTS

| | | |
|---|---|---|
| 3,485,416 A | 12/1969 | Fohrman |
| 3,869,062 A | 3/1975 | Jaeschke et al. |
| 3,934,722 A | 1/1976 | Goldberg |
| 4,184,593 A | 1/1980 | Dorr |
| 4,610,667 A | 9/1986 | Pedicano et al. |
| 4,795,432 A | 1/1989 | Karczmer |
| 4,813,940 A | 3/1989 | Parry |
| 4,950,242 A | 8/1990 | Alvarez |
| 4,950,250 A | 8/1990 | Haber et al. |
| 5,084,027 A | 1/1992 | Bernard et al. |
| 5,084,028 A | 1/1992 | Kennedy et al. |
| 5,330,899 A | 7/1994 | Devaughn |
| 5,336,197 A | 8/1994 | Kuracina et al. |
| 5,336,199 A | 8/1994 | Castillo et al. |
| 5,395,347 A | 3/1995 | Blecher et al. |
| 5,415,645 A | 5/1995 | Friend et al. |
| 5,591,138 A | 1/1997 | Vaillancourt |
| 5,688,241 A | 11/1997 | Asbaghi |
| 5,984,899 A | 11/1999 | D'Alessio et al. |
| RE36,885 E | 9/2000 | Blecher et al. |
| 6,880,701 B2 | 4/2005 | Bergeron et al. |
| 6,884,237 B2 | 4/2005 | Asbaghi |
| 6,926,697 B2 | 8/2005 | Malenchek |
| 7,134,550 B2 | 11/2006 | Groth |
| 7,320,682 B2 | 1/2008 | Cocker et al. |
| 7,361,159 B2 | 4/2008 | Fiser et al. |
| 7,513,888 B2 | 4/2009 | Sircom et al. |
| 7,665,605 B2 | 2/2010 | Erickson et al. |
| 7,811,261 B2 | 10/2010 | Rubinstein et al. |
| 7,871,397 B2 | 1/2011 | Schraga |
| 8,062,265 B2 | 11/2011 | Millerd |
| 8,133,200 B2 | 3/2012 | Dibiasi et al. |
| 8,162,882 B2 | 4/2012 | Rubinstein et al. |
| 8,303,541 B2 | 11/2012 | Chun |
| 8,333,738 B2 | 12/2012 | Millerd |
| 8,439,870 B2 | 5/2013 | Moyer et al. |
| 8,496,627 B2 | 7/2013 | Chelak et al. |
| 8,579,115 B2 | 11/2013 | Murphy et al. |
| 8,636,688 B2 | 1/2014 | Shaw |
| 8,636,703 B2 | 1/2014 | Foshee et al. |
| 8,647,307 B2 | 2/2014 | Gratwohl et al. |
| 8,663,129 B2 | 3/2014 | Allen et al. |
| 8,747,355 B2 | 6/2014 | Rubinstein et al. |
| 8,763,826 B1 | 7/2014 | Smith et al. |
| 8,827,961 B2 | 9/2014 | Emmott et al. |
| 8,968,241 B2 | 3/2015 | Liversidge |
| 8,979,794 B2 | 3/2015 | Chevallier |
| 9,050,416 B2 | 6/2015 | Feret et al. |
| 9,061,106 B2 | 6/2015 | Roberts et al. |
| 9,067,024 B2 | 6/2015 | Roberts et al. |
| 9,186,466 B2 | 11/2015 | Zachek et al. |
| 9,352,099 B2 | 5/2016 | Roberts et al. |
| 9,352,100 B2 | 5/2016 | Ward et al. |
| 9,352,101 B2 | 5/2016 | Roberts et al. |
| 9,370,327 B2 | 6/2016 | Teoh |
| 9,408,632 B2 | 8/2016 | Erskine |
| 9,445,760 B2 | 9/2016 | Allen et al. |
| 9,694,140 B2 | 7/2017 | Rubinstein et al. |
| 9,848,810 B2 | 12/2017 | Allen et al. |
| 2001/0031949 A1 | 10/2001 | Asbaghi |
| 2001/0051789 A1* | 12/2001 | Parsons ............... B65D 75/326 604/68 |
| 2002/0063074 A1 | 5/2002 | Simm et al. |
| 2002/0165497 A1 | 11/2002 | Greene |
| 2003/0015444 A1 | 1/2003 | Molin et al. |
| 2003/0093009 A1 | 5/2003 | Newby et al. |
| 2003/0120209 A1 | 6/2003 | Jensen et al. |
| 2003/0121815 A1 | 7/2003 | Bergeron et al. |
| 2003/0181867 A1 | 9/2003 | Bressler et al. |
| 2003/0181869 A1 | 9/2003 | Swenson et al. |
| 2004/0178098 A1 | 9/2004 | Swenson et al. |
| 2005/0067309 A1 | 3/2005 | Choi |
| 2005/0113750 A1 | 5/2005 | Targell |
| 2005/0119627 A1 | 6/2005 | Crawford |
| 2005/0279664 A1 | 12/2005 | Hommann |
| 2006/0189933 A1 | 8/2006 | Alheidt et al. |
| 2006/0189934 A1 | 8/2006 | Kuracina et al. |
| 2006/0213793 A1 | 9/2006 | Brand |
| 2009/0024093 A1 | 1/2009 | Carrel et al. |
| 2009/0254042 A1 | 10/2009 | Gratwohl et al. |
| 2009/0299295 A1 | 12/2009 | Rubinstein et al. |
| 2010/0298770 A1 | 11/2010 | Rubinstein et al. |
| 2011/0288491 A1 | 11/2011 | Newman et al. |
| 2011/0319817 A1 | 12/2011 | Rubinstein et al. |
| 2012/0029440 A1 | 2/2012 | Boyd et al. |
| 2012/0041380 A1 | 2/2012 | Chapin et al. |
| 2012/0051967 A1 | 3/2012 | Murphy et al. |
| 2012/0059331 A1 | 3/2012 | Dibiasi et al. |
| 2012/0130342 A1 | 5/2012 | Cleathero |
| 2014/0048433 A1 | 2/2014 | Dasbach et al. |
| 2014/0076758 A1 | 3/2014 | Dasbach et al. |
| 2014/0078854 A1* | 3/2014 | Head ............... B01F 11/0005 366/111 |
| 2014/0097111 A1 | 4/2014 | Dasbach et al. |
| 2014/0135706 A1 | 5/2014 | Rubinstein et al. |
| 2014/0228772 A1 | 8/2014 | Ward et al. |
| 2014/0364803 A1 | 12/2014 | Rubinstein et al. |
| 2015/0034516 A1 | 2/2015 | Chapin et al. |
| 2015/0094659 A1 | 4/2015 | Schraga |
| 2015/0165132 A1 | 6/2015 | Perot et al. |
| 2015/0182704 A1 | 7/2015 | Chevallier |
| 2015/0190580 A1 | 7/2015 | Imai et al. |
| 2015/0190586 A1 | 7/2015 | Takemoto |
| 2015/0197393 A1 | 7/2015 | Braun et al. |
| 2015/0297837 A1 | 10/2015 | Schraga |
| 2015/0297881 A1 | 10/2015 | Sanders et al. |
| 2016/0074572 A1 | 3/2016 | Spool et al. |
| 2016/0303331 A1 | 10/2016 | Evans et al. |
| 2017/0072142 A1* | 3/2017 | Perthu ............... A61M 5/46 |
| 2017/0106136 A1 | 4/2017 | Dibiasi |
| 2017/0233168 A1 | 8/2017 | Horvath et al. |
| 2018/0161490 A1 | 6/2018 | Sanders et al. |
| 2018/0161492 A1 | 6/2018 | Sanders et al. |
| 2018/0161521 A1 | 6/2018 | Sanders et al. |

FOREIGN PATENT DOCUMENTS

| | | |
|---|---|---|
| CN | 103079610 A | 5/2013 |
| EP | 0734739 A2 | 10/1996 |
| EP | 0750915 A2 | 1/1997 |
| EP | 1537890 A1 | 6/2005 |
| EP | 1949928 A1 | 7/2008 |
| EP | 2298397 A1 | 3/2011 |
| EP | 2585146 B1 | 3/2017 |
| FR | 2884723 A1 | 10/2006 |
| FR | 2930160 A1 | 10/2009 |
| GB | 2437923 A | 11/2007 |
| JP | 2007519474 A | 7/2007 |
| JP | 2013529973 A | 7/2013 |
| MX | 2013/000081 A | 3/2013 |
| MX | 349289 B | 7/2017 |
| WO | 92/06725 A1 | 4/1992 |
| WO | 02/11797 A1 | 2/2002 |
| WO | 03/045480 A1 | 6/2003 |
| WO | 2008050158 A2 | 5/2008 |
| WO | 2009040602 A1 | 4/2009 |
| WO | 2009/114777 A1 | 9/2009 |
| WO | 2010/033767 A2 | 3/2010 |
| WO | 2011/107330 A1 | 9/2011 |
| WO | 2012/000833 A1 | 1/2012 |
| WO | 2012000833 A1 | 1/2012 |
| WO | 2013073122 A1 | 5/2013 |
| WO | 2015/164416 A1 | 10/2015 |
| WO | 2016/087187 A1 | 6/2016 |

OTHER PUBLICATIONS

Final Office Action in U.S. Appl. No. 15/837,018 dated Jun. 18, 2019, 15 pages.

Final Office Action in U.S. Appl. No. 15/837,748 dated Feb. 29, 2020, 19 pages.

Final Office Action in U.S. Appl. No. 15/837,756 dated Feb. 28, 2020, 34 pages.

(56) References Cited

OTHER PUBLICATIONS

Final Office Action in U.S. Appl. No. 15/837,810 dated Feb. 28, 2020, 24 pages.
Non-Final Office Action in U.S. Appl. No. 15/837,008 dated Jul. 25, 2019, 23 pages.
Non-Final Office Action in U.S. Appl. No. 15/837,011 dated Oct. 7, 2019, 8 pages.
Non-final Office Action in U.S. Appl. No. 15/837,012 dated Aug. 16, 2019, 14 pages.
Non-Final Office Action in U.S. Appl. No. 15/837,018 dated Dec. 5, 2019, 14 pages.
Non-Final Office Action in U.S. Appl. No. 15/837,018 dated Nov. 6, 2018, 11 pages.
Non-Final Office Action in U.S. Appl. No. 15/837,020 dated Feb. 3, 2020, 11 pages.
Non-Final Office Action in U.S. Appl. No. 15/837,748 dated Oct. 17, 2019, 19 pages.
Non-Final Office Action in U.S. Appl. No. 15/837,756 dated Oct. 17, 2019, 39 pages.
Non-Final Office Action in U.S. Appl. No. 15/837,810 dated Oct. 17, 2019, 27 pages.
PCT International Preliminary Report on Patentability in PCT/US2017/065688 dated Jun. 27, 2019, 9 pages.
PCT International Preliminary Report on Patentability in PCT/US2017/065689 dated Jun. 27, 2019, 10 pages.
PCT International Preliminary Report on Patentability in PCT/US2017/065691 dated Jun. 27, 2019, 9 pages.
PCT International Preliminary Report on Patentability in PCT/US2017/065692 dated Jun. 27, 2019, 8 pages.
PCT International Preliminary Report on Patentability in PCT/US2017/065693 dated Jun. 27, 2019, 7 pages.
PCT international Preliminary Report on Patentability in PCT/US2017/065716 dated Jun. 27, 2019, 9 pages.
PCT International Preliminary Report on Patentability in PCT/US2017/065717 dated Jun. 27, 2019, 9 pages.
PCT International Preliminary Report on Patentability in PCT/US2017/065718 dated Jun. 27, 2019, 12 pages.
PCT International Search Report and Written Opinion in PCT/US2017/065688 dated Feb. 26, 2018, 13 pages.
PCT International Search Report and Written Opinion in PCT/US2017/065689, dated Jan. 2, 2019, 18 pgs.
PCT International Search Report and Written Opinion in PCT/US2017/065691 dated Mar. 27, 2018, 14 pages.
PCT International Search Report and Written Opinion in PCT/US2017/065692 dated Mar. 13, 2018, 14 pages.
PCT International Search Report and Written Opinion in PCT/US2017/065693 dated Mar. 7, 2018, 12 pages.
PCT International Search Report and Written Opinion in PCT/US2017/065716 dated Mar. 21, 2018, 14 pages.
PCT International Search Report and Written Opinion in PCT/US2017/065717 dated Mar. 19, 2018, 12 pages.
PCT International Search Report and Written Opinion in PCT/US2017/065718 dated Jan. 2, 2019, 18 pages.
PCT invitation to Pay Additional Fees and, Where Applicable, Protest Fee in PCT/US2017/065689 dated Feb. 20, 2018, 12 pages.
PCT invitation to Pay Additional Fees and, Where Applicable, Protest Fee in PCT/US2017/065718 dated Apr. 9, 2018, 13 pages.
Non-Final Office Action in U.S. Appl. No. 15/837,020, dated Jan. 29, 2021, 16 pages.
PCT International Search Report and Written Opinion in PCT/US2021/019381 dated Jun. 11, 2021, 18 pages.

\* cited by examiner

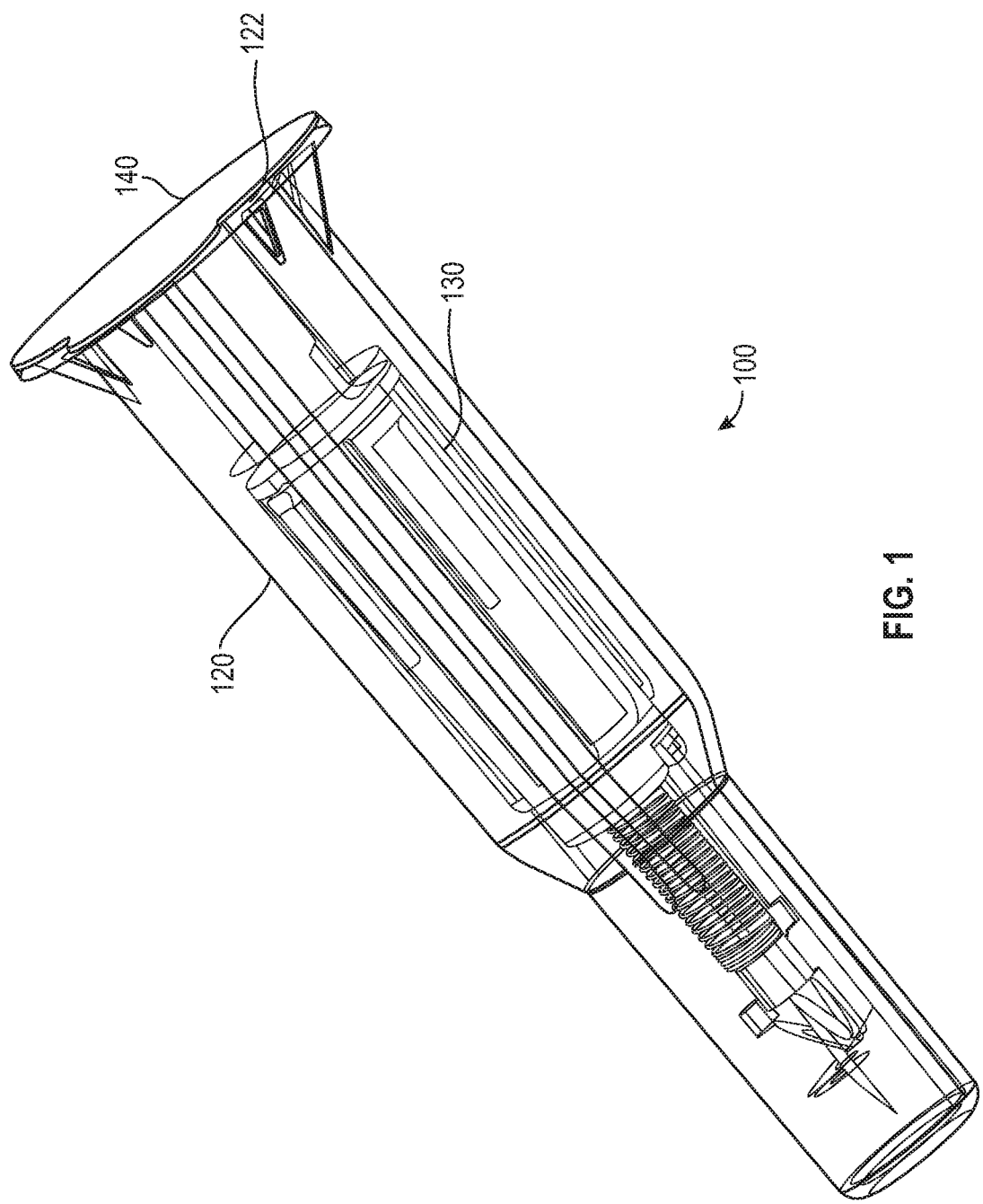

PACKAGING FOR SAFETY NEEDLE

CROSS-REFERENCE TO RELATED APPLICATIONS

This application is a continuation in part of U.S. patent application Ser. No. 15/837,018 filed Dec. 11, 2017 which claims priority under 35 U.S.C. § 119(e) to U.S. Provisional Application No. 62/433,044, filed Dec. 12, 2016, U.S. Provisional Application No. 62/479,507, filed Mar. 31, 2017 and U.S. Provisional Application No. 62/479,563, filed Mar. 31, 2017, the disclosures of which are incorporated herein by reference in their entirety.

TECHNICAL FIELD

The present disclosure generally relates to packaging for medical devices, and more particularly to dual packaging for passive safety needles requiring rotation of a tether or housing for passive activation.

BACKGROUND

Clean or sterile articles particularly useful for medical applications are packaged to preserve their sterility. The packaging for these articles is intended to provide a barrier to prevent microorganisms from entering inside the packaging to contaminate its contents. In most instances, the packaging is opened immediately prior to using the article, such as with a blister pack housing a syringe or a needle, so as to minimize the time period in which the article is exposed to unsterile conditions.

Traditionally, practitioners that fill and inject syringes can use a one or two-needle technique. In the one-needle technique, the practitioner fills the syringe from a container (e.g. vial) having a liquid contained therein, and uses the same needle for injection. In the two-needle technique, the practitioner fills the syringe with a first needle, but replaces the needle with a new needle prior to injecting.

Both the one-needle technique and the two-needle technique offer certain advantages and disadvantages. For example, the one-needle technique is convenient because the practitioner does not have to change needles between filling and injection, but the needle can become contaminated between filling and injection. The two-needle technique allows for specialized needles that are optimized for filling and injection, but is more cumbersome for the practitioner.

Accordingly, there is a need for alternative packaging systems for providing needles to a user in a sterile condition. There is also a need to provide packaging to prevent unintended activation for passive safety needles that requiring rotation of a tether or housing for passive activation.

SUMMARY

One aspect of the present disclosure pertains to a packaging system comprising a safety needle device having a tether and a retractable sleeve. The tether includes a recess disposed on a distal end of the tether, and the retractable sleeve advanceable within the tether. The packaging system further includes a hard package having a closed distal end, an open proximal end, and a compartment extending between the closed distal end and the open proximal end. A premature activation prevention element of the compartment nests within the recess of the safety needle device. A removable seal is disposed against the open proximal end, wherein the compartment and the removable seal define a sealed region, the safety needle device being disposed within the sealed region. In one or more embodiments, the safety needle device is a passive safety needle or an active safety needle.

In one or more embodiments, the premature activation prevention element comprises at least one rail, the at least one rail having a protruding ledge extending from an inner sidewall of the compartment, the protruding ledge extending toward the center of the compartment.

In one or more embodiments, the protruding ledge has a width that is slightly less than the width of the recess of the safety needle device. The protruding ledge prevents rotation of the safety needle device when the safety needle device is disposed within the compartment.

A second aspect of the present disclosure pertains to a packaging system comprising a safety needle device having a tether and a retractable sleeve. The tether includes a recess disposed on a distal end of the tether, and the retractable sleeve advanceable within the tether. The packaging system further includes a hard package comprising a first compartment, and a second hard package having a closed distal end, an open proximal end, and a second compartment extending between the closed distal end and the open proximal end. A premature activation prevention element disposed on an inner sidewall of the compartment removably nests within the recess of the tether of the safety needle device. The premature activation prevention element being at least one rail having a protruding ledge which nests within the recess of the safety needle device. A removable seal is disposed against the open proximal end, wherein the compartment and the removable seal define a sealed region, the safety needle device being disposed within the sealed region. A second removable seal is sealed against the second compartment. The second removable seal defines a second sealed region in which the safety needle is disposed within. The first hard package is attached to the second hard package.

In one or more embodiments, the least one rail disposed on an inner sidewall of the compartment extends from a closed distal end of the compartment at least partially the length of the compartment.

In one or more embodiments, the least one rail is disposed on an inner sidewall of the compartment extends from a closed distal end of the compartment to the open proximal end.

In one or more embodiments, the least one rail has a width that is less than a width of the recess of the safety needle device.

In one or more embodiments, the first hard package is connected to the second hard package via press fitting, an adhesive bond, a solvent bond, a ring connector, a snap fit, a C-clip snap, heat staking or ultrasonic welding.

In one or more embodiments, the first hard package has a perforated attachment to the second hard package.

In one or more embodiments, the first removable portion comprises a first pull tab and the second removable portion comprises a second pull tab.

In one or more embodiments, the first removable seal includes graphics, symbols, diagrams, words or instructions to indicate that the first removable seal is to be opened first.

In one or more embodiments, the second removable seal includes graphics, symbols, diagrams, words or instructions to indicate that the first removable seal is to be opened second.

In one or more embodiments, the first hard package has a first color and the second hard package has a second color.

A third aspect of the present disclosure pertains to a packaging system having a needle, a safety needle device, and a blister package having a first cavity and a second cavity. The second cavity has a premature activation prevention element to nest within the recess of the safety needle device. The first and second cavities are sealed against a backing, the first cavity and the backing defining a first sealed region, and the second cavity and the backing defining a second sealed region. A distal end of the needle being disposed within the first sealed region and a distal end of a second needle being disposed within the second sealed region.

In one or more embodiments, the needle is a blunt fill needle.

In one or more embodiments, the safety needle device is a passive safety needle or an active safety needle.

In one or more embodiments, the recess has a width that is slightly larger than a width of the protruding activation element of the compartment, the protruding activation element preventing rotation of the safety needle device when the protruding activation element is nested within the recess.

In one or more embodiments, a cap is disposed about the distal end of the needle.

In one or more embodiments, the blister package includes a peel tab.

BRIEF DESCRIPTION OF THE DRAWINGS

FIG. 1 illustrates a single packaging for a safety needle device;

DETAILED DESCRIPTION

Figure 2A:
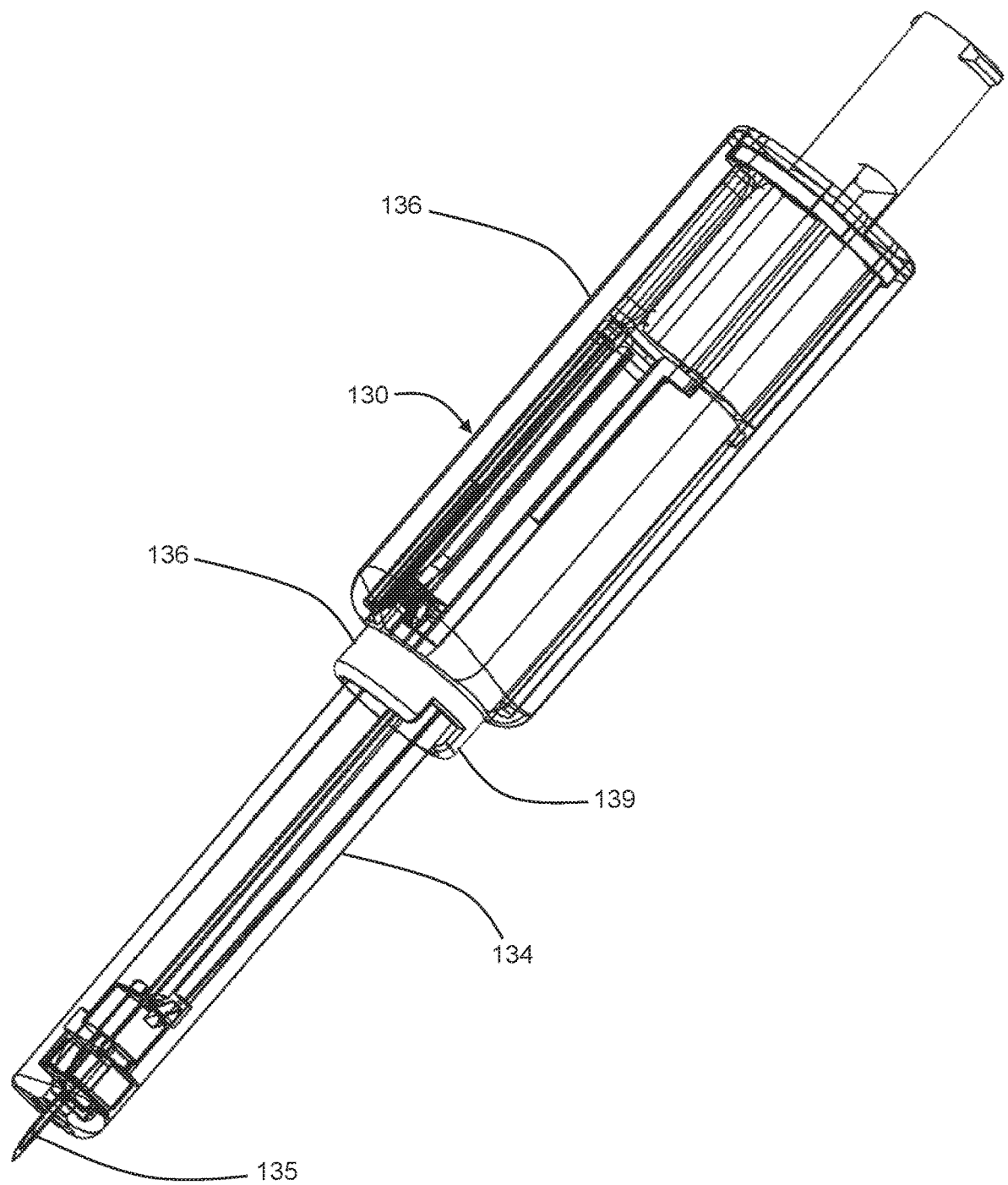
FIGS. 2A and 2B illustrate a safety needle device of FIG. 1.

Before describing several exemplary embodiments of the present disclosure, it is to be understood that the embodiments of the present disclosure are not limited to the details of construction or process steps set forth in the following description. The embodiments of the present disclosure are capable of other embodiments and of being practiced or being carried out in various ways.

With respect to terms used in this disclosure, the following definitions are provided.

As used herein, the use of "a," "an," and "the" includes the singular and plural.

Reference to "needle" includes needles that are suitable for filling and/or injecting liquids into or out of a syringe. In this disclosure, a convention is followed wherein the portion of a needle closest to the practitioner operating the needle is termed "proximal" and the portion of the needle toward the patient (for injection) or vial containing liquid (for filling) and farthest from the practitioner is termed "distal." In various embodiments, the needles described herein can be blunt fill needles, safety needles and/or conventional needles.

As used herein, a "fill needle" refers to a needle that is suitable to fill a syringe but may not be suitable for injection. For example, a fill needle may be a blunt needle that is not suitable to penetrate a patient's skin.

As used herein, a "safety needle" refers to a needle suitable for injection that includes one or more features to prevent needle stick injuries. In one or more embodiments, a safety needle includes a sheath that covers the distal end of the needle. As used herein, an "active safety needle" refers to a safety needle with a user-operated activation mechanism to cover the distal end of the needle after a patient has been injected. As used herein, a "passive safety needle" refers to a safety needle with a passive activation mechanism that automatically covers the distal end of the needle after a patient has been injected.

Any suitable needle devices comprising a safety feature may be used in conjunction with the packaging disclosed herein. Exemplary safety needle devices include, but are not limited to, those described in commonly owned, U.S. Patent Application Nos. 62/433,294, 62/433,350, 62/479,507, 62/533,786, the disclosures of which are incorporated herein by reference in their entireties. Types of safety features vary in structure and mechanics but in general, safety needle devices have a fill state and an inject state.

Reference to "syringe" includes syringes that are indicated for use with needles, nozzle, tubing, or for use in flush systems. As used herein, the term "syringe" refers to a simple pump-like device consisting of a plunger rod that fits tightly in a barrel or tube. The plunger rod can be pulled or pushed along inside the barrel, allowing the syringe to take in and expel a liquid or gas through an opening at the open end of the barrel. The open end of the syringe may be fitted with a needle, nozzle, or tubing to help direct the flow of fluid into and out of the barrel. The syringe may be sterile or unsterile, depending upon the needs of the technician.

As used herein, the terms "package" or "packaging" includes any material used to wrap or protect a good or product, such as a syringe or a needle. Packaging can be rigid or flexible. Packaging includes, but is not limited to, medical packaging, pharmaceutical packaging, and child-resistant packaging. Medical and pharmaceutical packaging can include blister packs or hard packages.

As used herein, the terms "blister package" or "blister pack" includes several types of pre-formed packaging used for consumer goods, foods, pharmaceuticals, medical devices, etc. The primary component of a blister pack is a cavity or pocket made from a formable web, usually a thermoformed plastic. The formable web can be rigid or flexible. The cavity or pocket is large enough to contain the good which is housed in the blister package. Depending on the application, a blister pack may have a backing of thermoformable material and a lidding seal of aluminum foil, paper, Tyvek®, plastic, or other medical grade materials. Blister packs can also be hinged, clamshell containers, that can include a rigid backing, such as paperboard. Blister packages can provide barrier protection from microorganisms and other contaminants, and can provide a certain degree of tamper resistance. Within the many options that blister packaging provides, the blister pack must protect the product contained inside while still possessing the characteristic capable of making automated processing possible.

Blister packs are commonly used as unit-dose packaging for pharmaceutical tablets, capsules, or lozenges. The pharmaceutical product and its blister pack act together to serve as an integral unit. The blister pack protects the pharmaceutical product from outside influences that would otherwise render it useless while allowing the manufacturer of the pharmaceutical product to package it using form-fill-seal equipment. The form-fill-seal process involves creating the blister pack from rolls of flat sheet or film, filling with the pharmaceutical product, such as a drug tablet, and closing (sealing). This type of blister pack is sometimes referred to as push-through-packs because the consumer can push the good (e.g. drug tablet) through the backing. With pharmaceutical blister packs, manufacturers must be concerned with the moisture vapor transmission rate of the blister pack because many pharmaceutical products degrade and lose their efficacy through hydrolysis. Additionally, the blister pack must provide a barrier to oxygen in order to prevent degradation of the pharmaceutical product through oxidation. In one or more embodiments, the blister pack is a push-through-pack.

Blister packages that contain medical devices, such as a syringe, differ from pharmaceutical blister packs because medical blister packs are not push-through packages. Instead, the thermoformed base web is made of a thicker plastic and cannot be collapsed, thus forming a solid backing. The lidding film provides a peel-open feature that can be peeled open using two-hands, such as, e.g. the knuckle-roll-peel technique. The lidding film of a medical blister pack is generally porous to allow sterilization. Often, medical blister packs are made of Tyvek® or a similar medical grade material that is breathable and permeable to gases, but is not permeable to microorganisms. The lidding film can also be made of medical grade paper or a completely non-permeable or non-breathable film. In instances where a non-breathable film is used, sterilization is through radiation (e.g. electron beams (E-beam)). In one or more embodiments, the blister pack is a medical blister pack.

Blister packs can be created via thermoforming or cold forming. In the case of thermoforming, a plastic film or sheet is unwound from a reel and guided through a pre-heating station on the blister line. The temperature of the pre-heating plates is such that the plastic will soften and become pliable. The warm plastic then arrives in a forming station where a large pressure forms the blister cavity into a negative mold. The mold is cooled such that the plastic becomes firm again and maintains its shape when removed from the mold.

In the case of cold forming, an aluminum based-laminate film is simply pressed into a mold by means of a stamp. The aluminum elongates and maintains the formed shape. The use of aluminum offers a complete barrier for water and oxygen. However, cold form blister packs take longer to produce compared to thermoforming. Cold form blister packs are also not transparent, which can lead to consumers not complying with pharmaceutical therapies.

The thermoformable backing of the medical blister pack is generally comprised of a flexible thermoformable plastic film. The film is often multi-layered. The primary component is regularly a layer of approximately 15-30% Nylon, while the remaining layers can comprise substances including, but not limited to, polyethylene. The sealant layer can comprise, among others, ethyl vinyl acetate (EVA).

The lidding film of a medical blister pack can be made from plastic, aluminum, or medical grade papers that are permeable to gases for sterilization but are impermeable to microorganisms. Most commonly, Tyvek® is used as a lidding material for medical blister packs.

Blister packaging can also include the skin pack, where a paperboard or other backing material and product are covered with a thin sheet of transparent plastic. The backing generally has a heat-seal coating. The plastic film is softened by heat and draped over the product on the backing. Vacuum is sometimes used to assist in a snug fit. Immediately after forming the blister, the blister is transported to a vacuum sealing station where a vacuum is pulled and the blister is sealed shut, providing the snug fit. The plastic film bonds to the heat-seal coating on the paperboard or other backing. In one or more embodiments, the blister pack is a vacuum sealed thermoformed blister pack.

Blister packs can be sealed in a variety of ways including, but not limited to, heat-sealing and cold sealing. Lidding materials can have a heat-seal coating applied to them; the lidding is then sealed to the backing using heat, which activates the coating. Blister packs can also be sealed using a cold seal process, which uses a combination of a pressure sensitive fold-over blister card and a transparent blister; the blister is trapped between two pieces of board that are bonded together under pressure without using any heat. Additionally, blister packs can be sealed by orienting multiple layers of film properly in order to make a seal.

As used herein, the term "hard package" or the like includes packaging having a compartment with one or more openings that can be covered to create a seal. In one or more embodiments, the hard package includes one or more components made of a rigid material such as a rigid polymeric material. Examples of rigid polymeric materials include, but are not limited to, polyester, polycarbonate, polyethylene, polystyrene or polypropylene, or combinations or co-polymers thereof. In one or more embodiments, a hard package can thermoformed or molded, such as by injection molding. The techniques described above for blister packs can be applied to the rigid portions of hard packages and/or to removable portions of hard packages.

As used herein, the term "microorganism" refers to a microbe or organism that is unicellular or lives in a colony of cellular organisms. Microorganisms are very diverse; they include, but are not limited to, bacteria, fungi, archaea, and protozoans.

Tyvek® is a synthetic material consisting of flashspun high-density polyethylene fibers (i.e. a spunbound olefin fiber). The material is lightweight and strong, and is resistant to tearing but can be cut with scissors or a knife. Water vapor and other gases can pass through Tyvek® as the material is highly breathable, but, at the same time, the material is impermeable to liquid water and microorganisms.

As used herein, the term "sterilization" refers to a means of eliminating or killing microorganisms present on a surface, contained in a fluid or in a compound such as biological culture media in order to achieve asepsis or a sterile microbial environment. Sterilization can be achieved by applying heat, chemicals, irradiation/radiation, high pressure, filtration, or combinations thereof. Chemical sterilization includes sterilization with gases such as ethylene oxide, hydrogen peroxide gas, and ozone, liquids such as chlorine bleach, iodine, glutaraldehyde and formaldehyde, ortho-phthaladehyde (OPA), hydrogen peroxide, peracetic acid, sodium hydroxide, silver, and cobalt. Radiation sterilization involves the use of radiation such as electron beams (E-beam), x-rays, gamma rays, or subatomic particles.

As used herein, the term "knuckle-roll-peel technique" refers to the process whereby a technician, such as a doctor or nurse, opens a package to release the product contained therein. With a knuckle-roll motion, the outer packaging material is peeled apart using two hands, and the inner product is released.

Various embodiments of the present disclosure provide dual packaging systems containing two needles. In one or more embodiments, this dual packaging can help to improve work flow and efficiency for users of the two-needle technique by removing the need to remember to get two needles instead of one. In one or more embodiments, this dual packaging can also be helpful for clinicians who traditionally use a one-needle technique to fill and inject, as such practitioners may not be used to getting a separate packaged component. In one or more embodiments, this dual packaging can also help to drive compliance in clinical settings where managers want clinicians to use a two-needle technique but the clinicians would prefer to use the more convenient one-needle technique. In one or more embodiments, dual packaging can be beneficial because it helps to prevent a user from injecting a patient with a device in the fill state either accidentally or purposefully. For passive safety, injection with a device in a fill state could prevent the safety from activating. In one or more embodiments, providing two needles allows a user to perform injection with a second needle that has not been dulled, recapped, or undergone risk of touch contamination. In one or more embodiments, the two needles include a fill needle (e.g. blunt fill needle) and a needle for injection (e.g. a safety needle). In other embodiments, one or both of the needles is a conventional needle.

One or more embodiments of the present disclosure relate to a single compartment or dual compartment packaging system having a hard package.

FIG. 1 illustrates an exemplary embodiment of a single compartment packaging system 100. As illustrated, compartment 120 can house a safety needle device 130. A removable seal 140 disposed against the open proximal end 122. As shown in FIG. 1, the compartment 120 can be molded in a single piece, such as by injection molding.

Figure 2B:
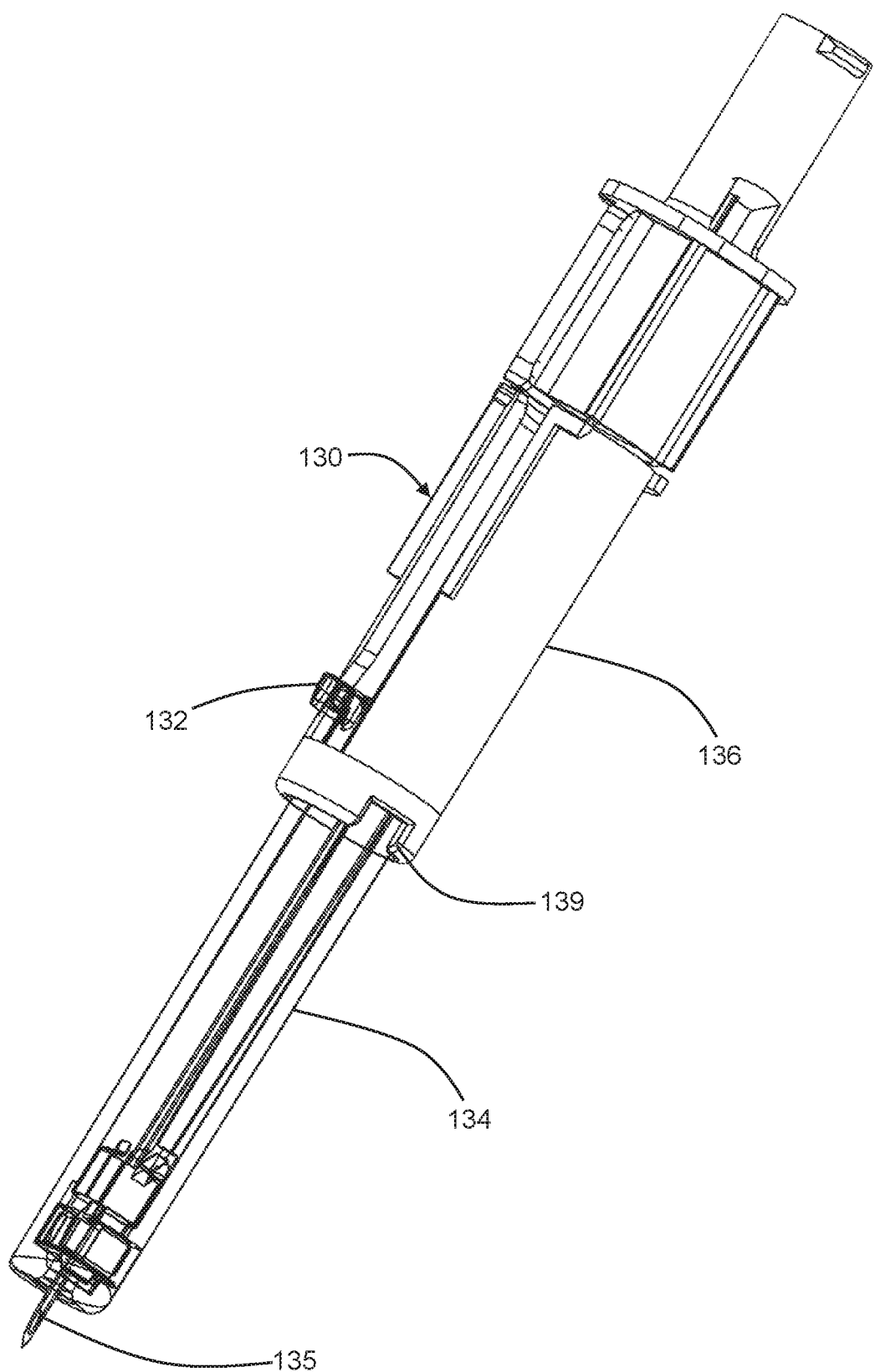
Figure 3A:
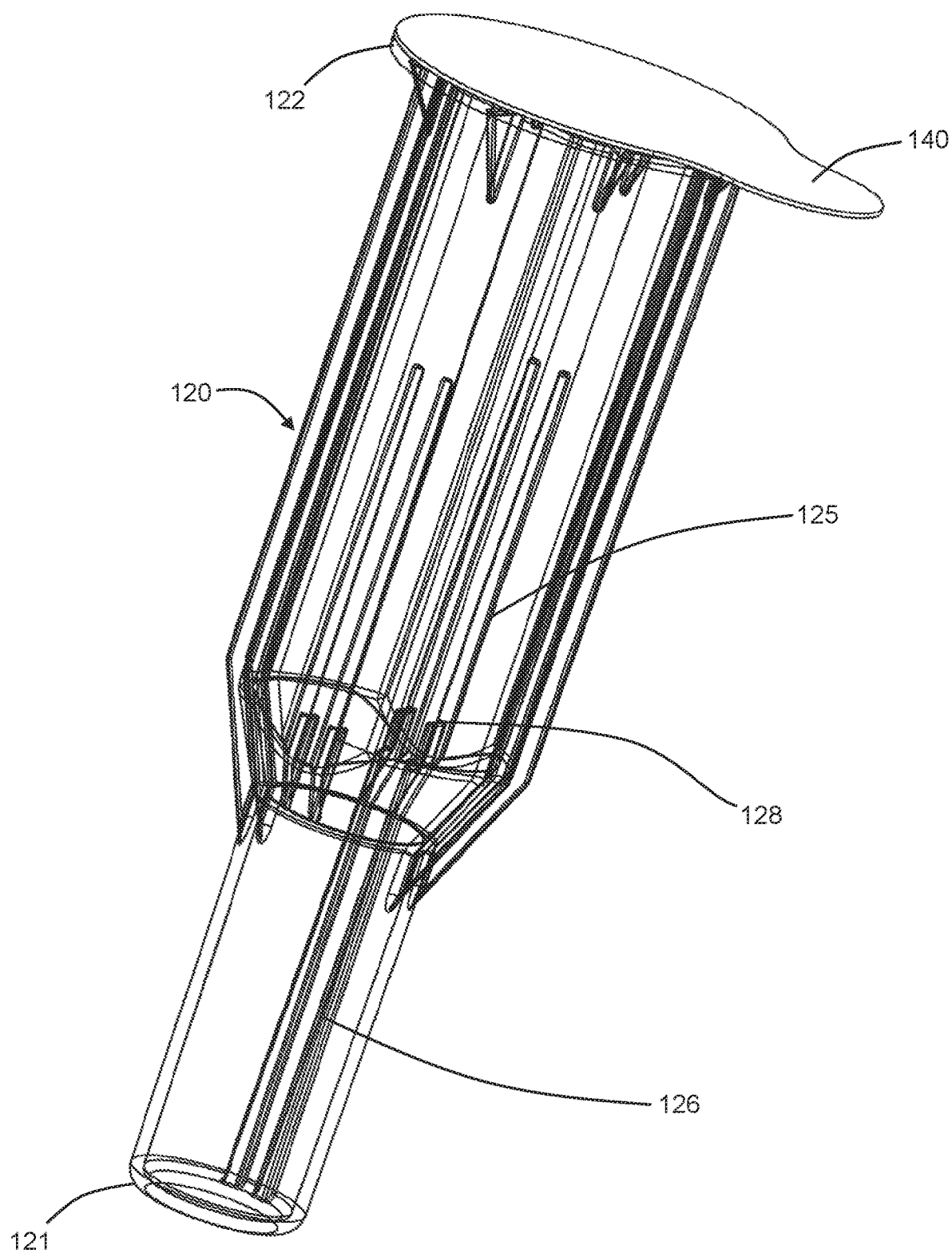
FIG. 3A illustrates a compartment of the single packaging of FIG. 1.
Figure 3B:
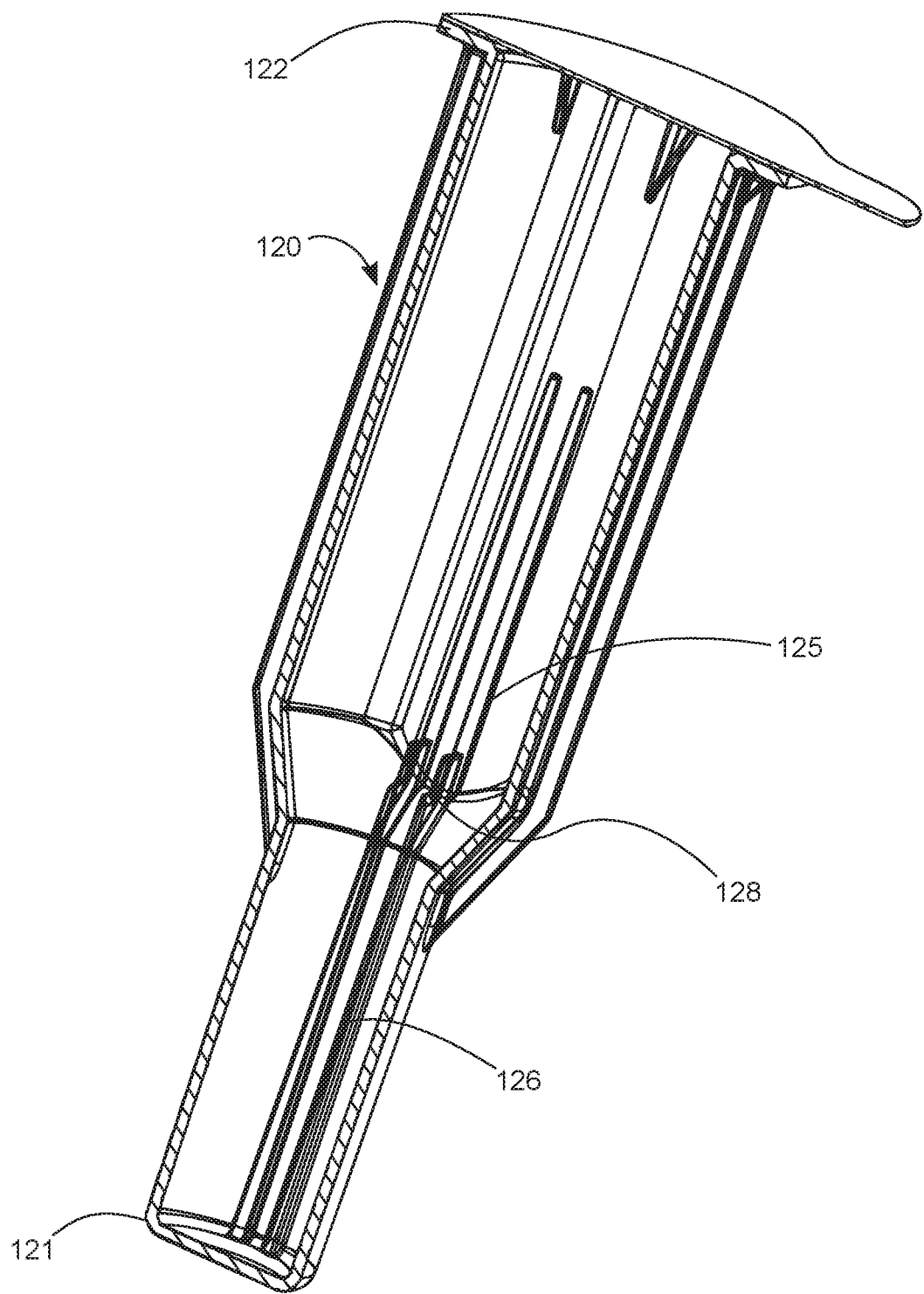
FIG. 3B illustrates a section view of the compartment of the single packaging of FIG. 1.
Figure 3C:
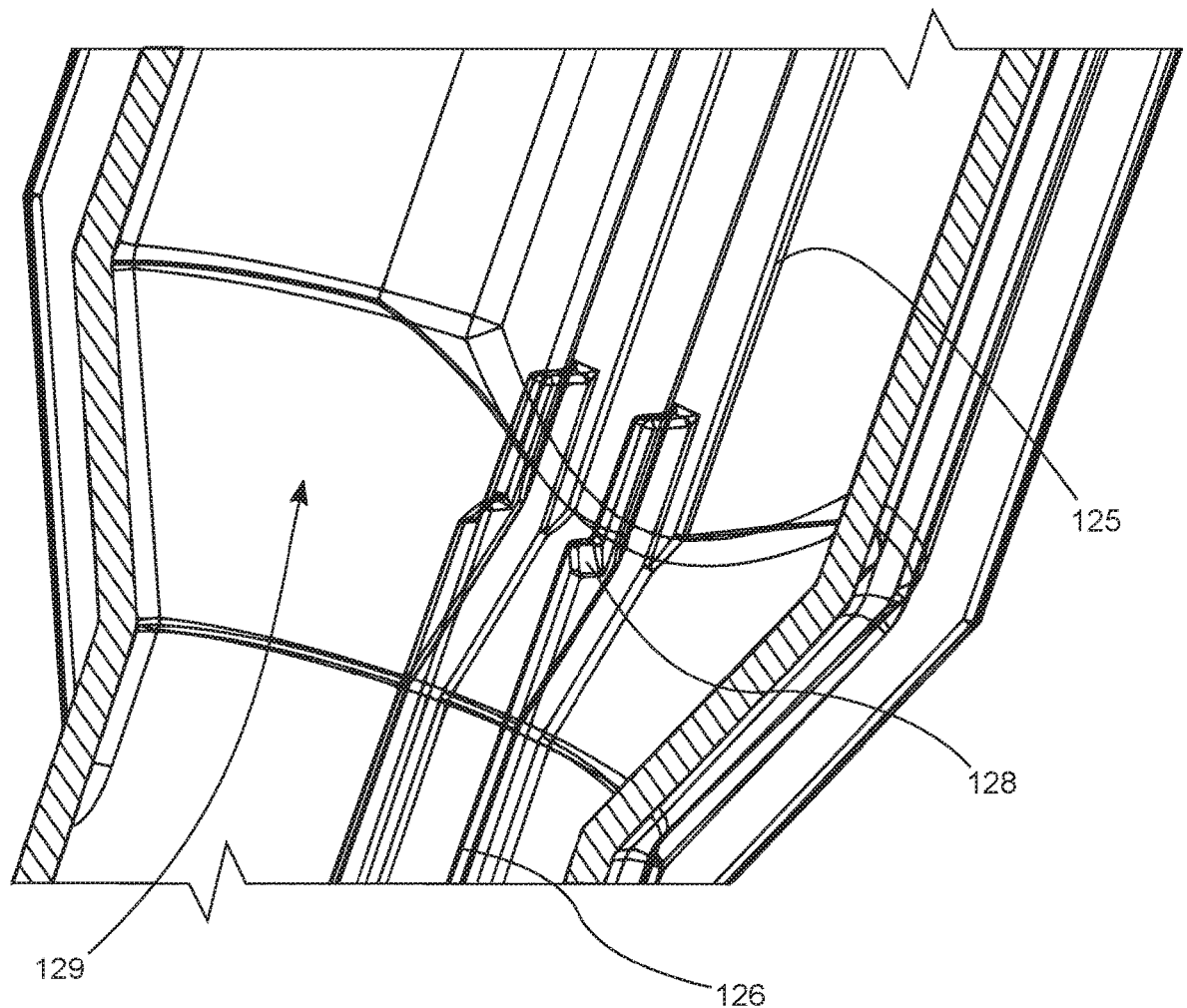
FIG. 3C illustrates a detailed section view of the compartment of the single packaging of FIG. 1.
Figure 4A:
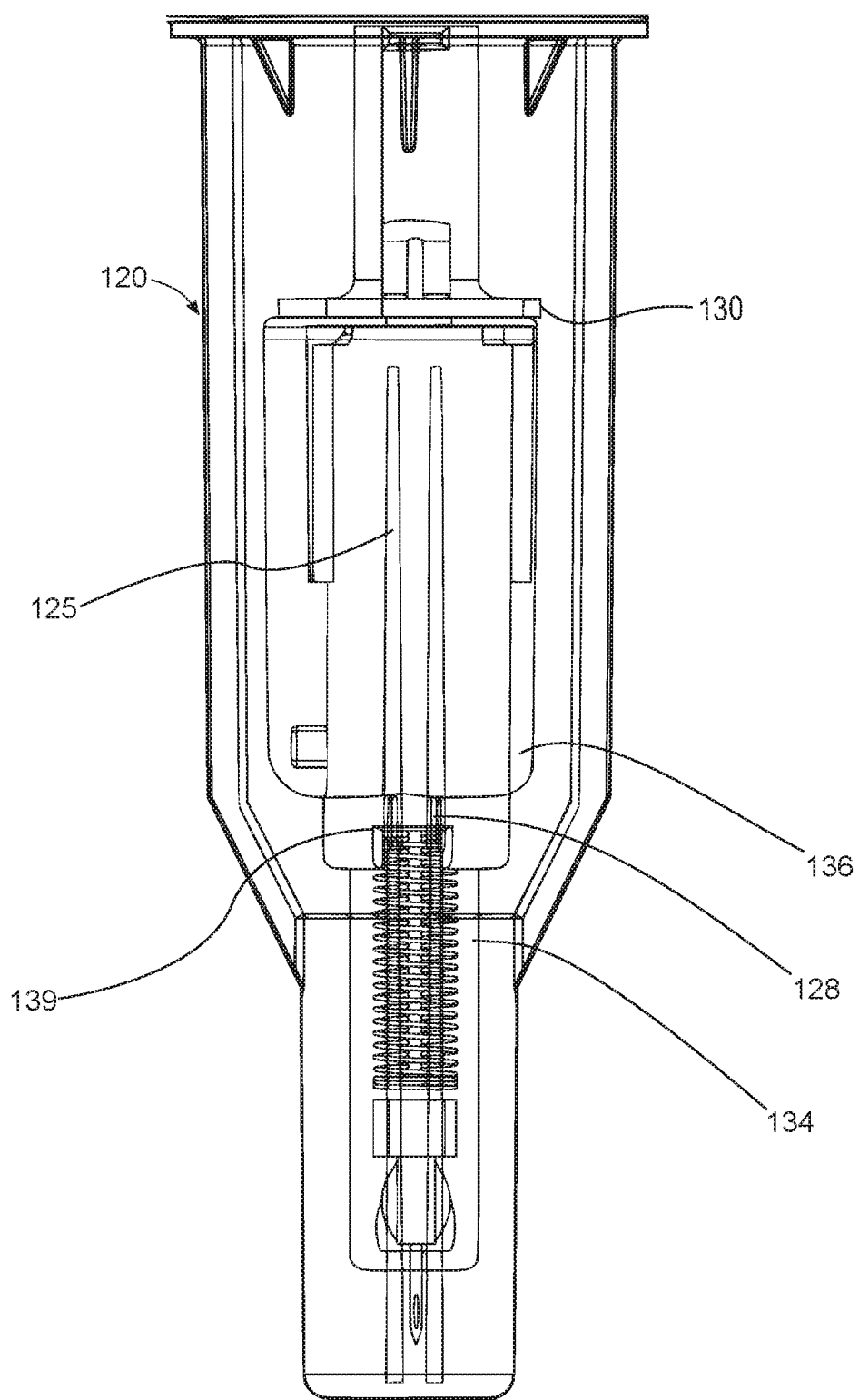
FIG. 4A illustrates the safety needle device disposed within the compartment of the single packaging of FIG. 1.
Figure 4B:
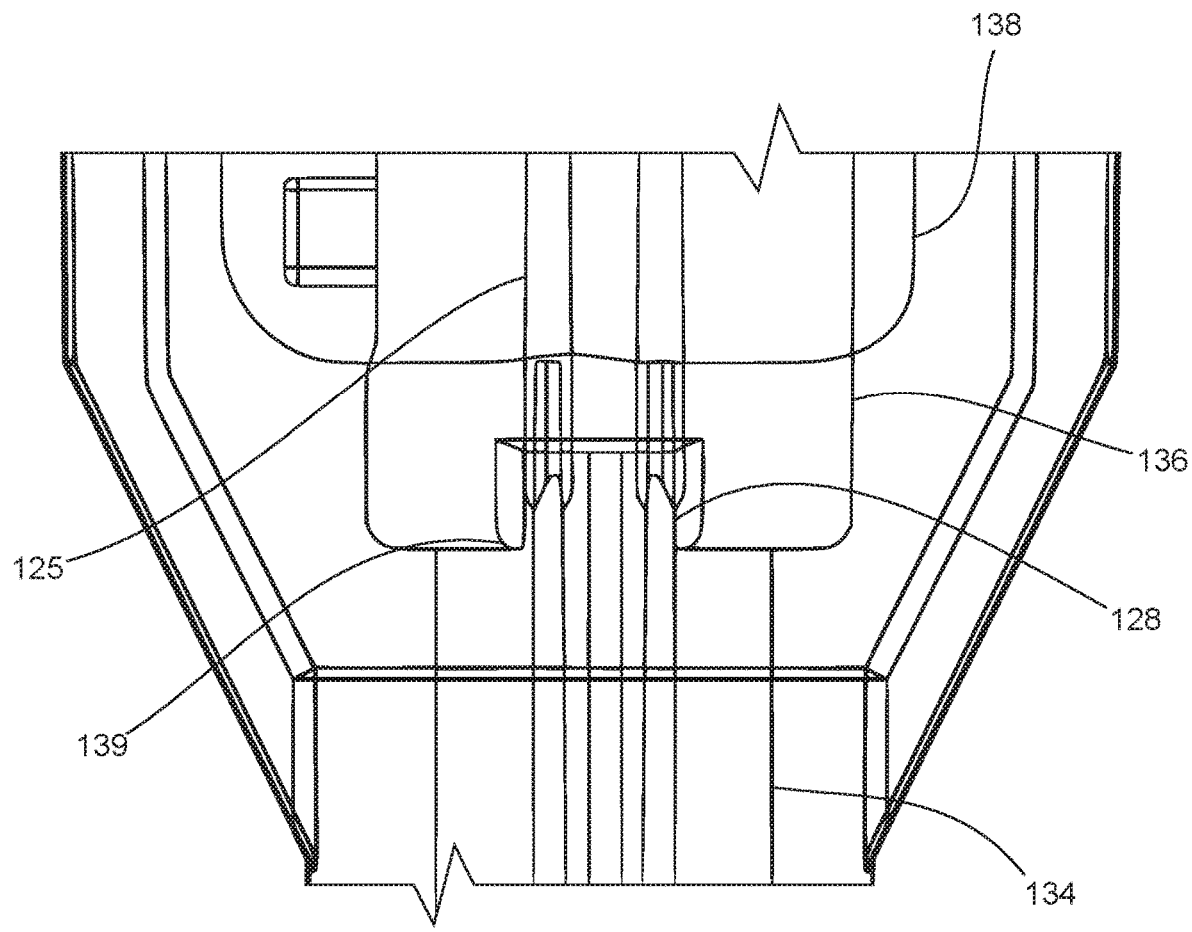
FIG. 4B illustrates a detailed view the safety needle device disposed within the compartment of the single packaging of FIG. 1.
Figure 4C:
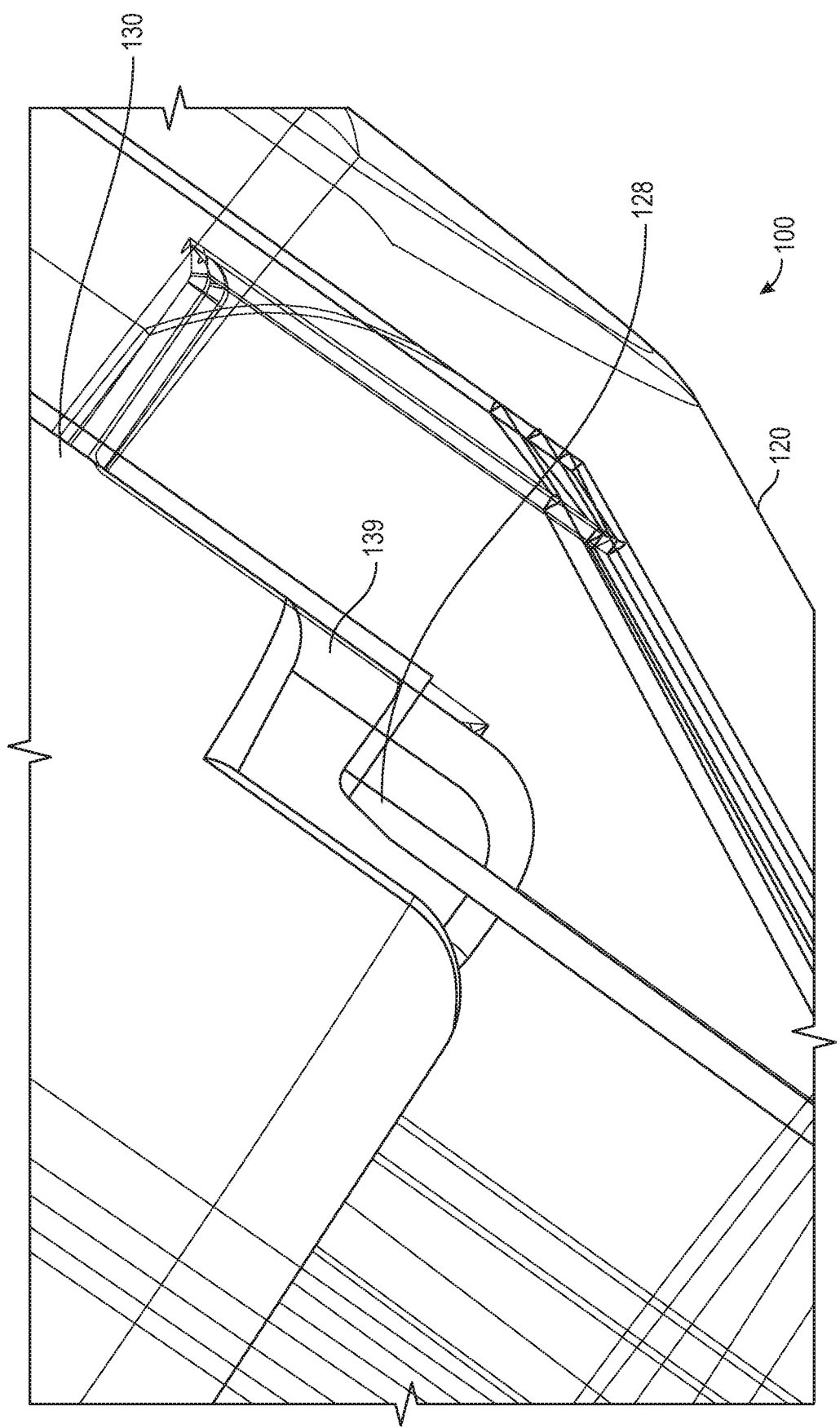
FIG. 4C illustrates a detailed side perspective view the safety needle device disposed within the compartment of the single packaging of FIG. 1.
Figure 4D:
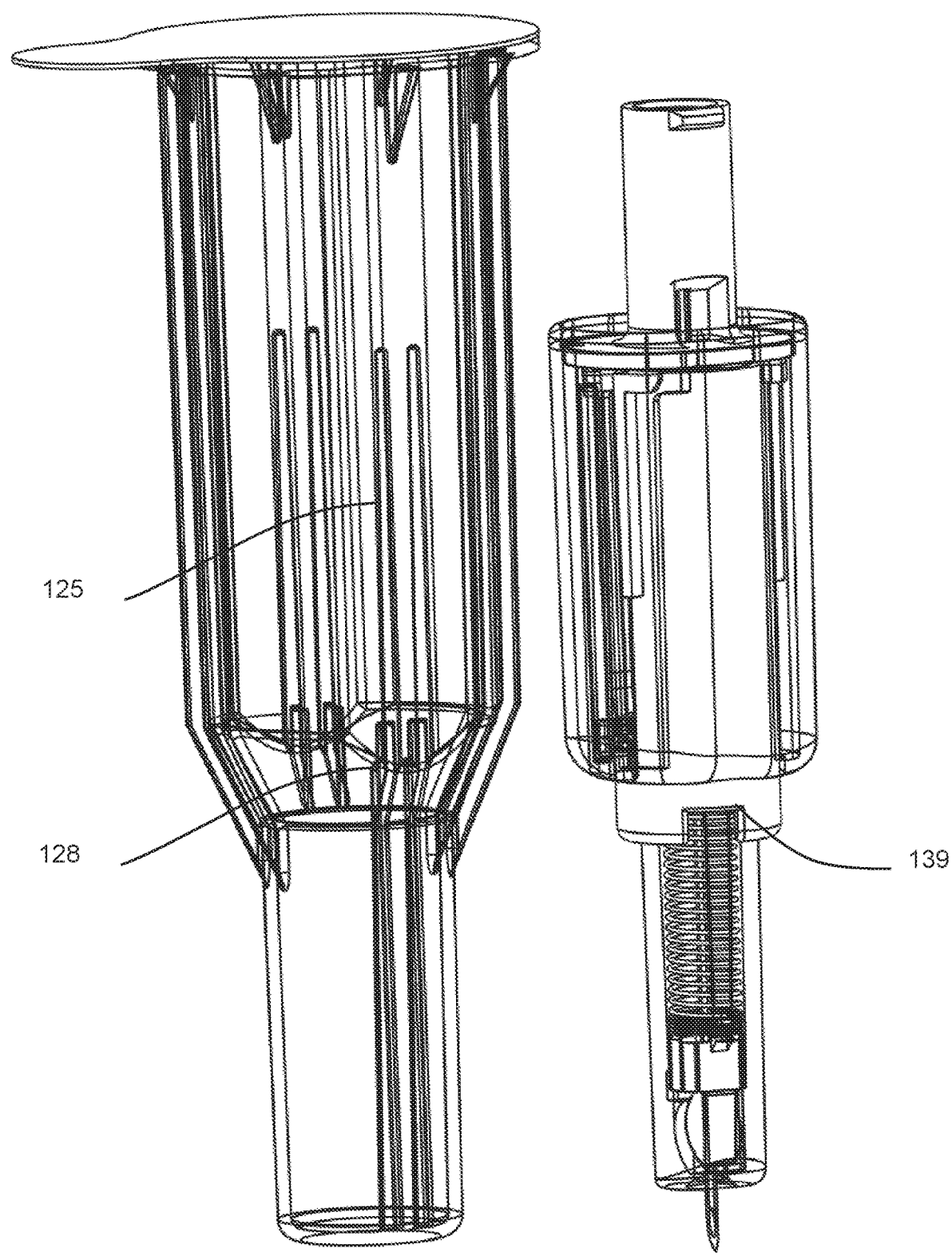
FIG. 4D illustrates an exploded view of the safety needle device and the single compartment of FIG. 1.

FIGS. 2A and 2B illustrate a safety needle device 130 comprising a retractable sleeve 134 having a protruding activation element 132 advanceable within a tether 136, the retractable sleeve and tether 136 being disposed within a housing 138. The retractable sleeve at least partially covers a needle 135 in an initial state. The tether 136 includes a recess 139 disposed on a distal end of the tether. As disclosed in further detail below, the recess 139 of the tether 136 interdigitates with a premature activation prevention element 125, as shown in FIGS. 3A-3C of the compartment 120 to prevent inadvertent activation of the retractable sleeve 134 during transportation, storage or packaging generally. For purposes of illustration, in FIG. 2B, the housing 138 has been removed for purposes of clarity. In one or more embodiments, the protruding activation element 132 is integral with the retractable sleeve 134. In one or more embodiments, the safety needle device 130 is a passive safety needle. In one or more embodiments, the safety needle device 130 is an active safety needle.

As shown in FIG. 3A-3C, the single compartment packaging system 100 may include a hard package having a closed distal end 121, an open proximal end 122, and a compartment 120 extending between the closed distal end 121 and the open proximal end 122. A removable seal 140 disposed against the open proximal end 122. Compartment 120 and removable seal 140 define a sealed region in which the safety needle device 130 is disposed. The removable seal 140 can be a pull tab.

As shown in FIG. 3B-3C, the compartment 120 includes a premature activation prevention element 125 which nests within the recess (not shown) of the safety needle device 130. In the preferred embodiment, the premature activation prevention element 125 includes at least one rail 126 disposed on an inner sidewall 129 of the compartment 120 extending from the closed distal end 121 at least partially the length of the compartment. In one or more embodiments, the at least one rail 126 extends to the open proximal end. The at least one rail 126 has a width that is less than a width of the recess 139 of the safety needle device 130. In one or more embodiments, the premature activation prevention element 125 comprises two parallel rails, the two parallel rails having a distance between them wherein the two parallel rails are configured to nest within the width of the recess 139 of the safety needle device 130. In one or more embodiments, premature activation prevention element 125 comprises a single unitary rail.

As shown in FIG. 3C, the at least one rail 126 includes a protruding ledge 128. The protruding ledge 128 protrudes towards the center of the compartment 120. The protruding ledge 128 is configured to nest within the recess 139.

As shown in FIGS. 4A-4D, the safety needle device 130 is disposed within the compartment 120. For purposes of clarity, a spring of the safety needle device 130 has been obscured from view in order to better illustrate the protruding ledge 128 of the premature activation element 125 being nested within the recess 139 of the safety needle device 130. When the safety needle device 130 is disposed within the compartment 120, the protruding ledge 128 of the premature activation prevention element 125 of the compartment 120 is nested within the recess 139 of the housing 138 of the safety needle device 130. The premature activation element 125 of the compartment 120 prevents premature or inadvertent activation of the safety needle device 130 by preventing rotation of the safety needle device 130. Due to the at least one rail 126 of the premature activation element 125 having a width that is less than the width of the recess 139 of the tether 136, the protruding ledge 128 sits within the recess 139. In one or more embodiments, the width of the at least one rail 126 is slightly less than the width of the recess 139, thereby allowing only minimal rotation, but not free rotation of the safety needle device 130 within the compartment 10.

Figure 5:
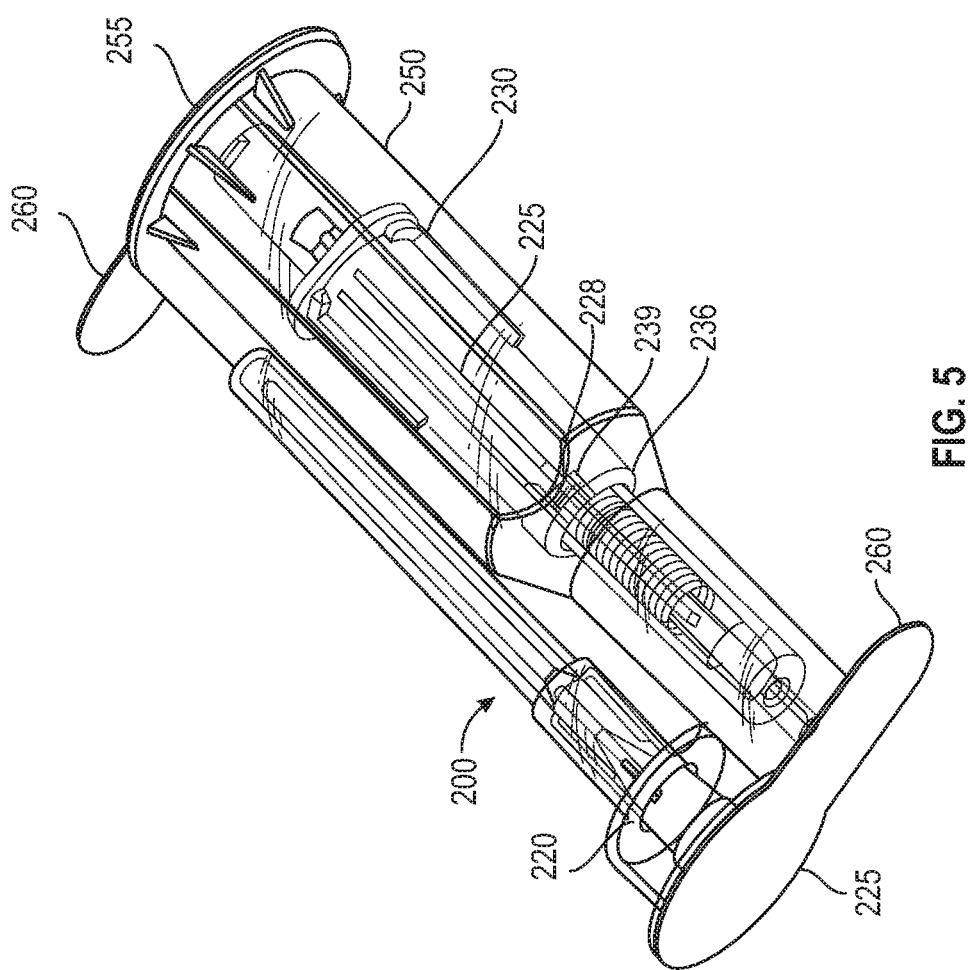
FIG. 5 illustrates a dual packaging with two pull tabs.

FIG. 5 illustrates an exemplary embodiment of a dual packaging system 200. The packing system has a first compartment 220 that can house a first needle and a second compartment 250 that can house a safety needle device 230. As shown in FIG. 3, the first compartment 220 and second compartment 250 can be molded in a single piece, such as by injection molding.

The first compartment 220 has an opening that is covered by a first removable seal 225. The first removable seal 225 is sealed against the first compartment 220, with the first compartment 220 and the first removable seal 225 defining a first sealed region. The first removable seal 225 can include a pull tab for a user to grab in order to remove the first removable seal 225 to access the first compartment 220.

In one or more embodiments, the first removable seal 225 can include graphics, symbols, diagrams, words or other instructions to indicate that it is to be opened first. For example, the first removable seal 225 can include the number "1". The first removable portion may also include graphics, symbols, diagrams, words or other instructions to indicate the intended use of the needle stored in the first compartment 220. In one or more embodiments, the first removable seal 225 can include graphics, symbols, diagrams, words or other instructions to indicate that it is to be opened first.

The second compartment 250 has an opening that is covered by a second removable seal 255. Second compartment 250 includes a premature activation prevention element 235 disposed within the compartment that can nest a recess 239 disposed on a distal end of a tether 236 of the safety needle device 230. In one or more embodiments, the premature activation prevention element 235 is in the form of at least one rail 226 disposed on an inner sidewall of the compartment 250. In one or more embodiments, the premature activation prevention element 225 interdigitates with the recess 239 of the protruding activation element 232. The at least one rail 226 includes a protruding ledge 228. The protruding ledge 228 protrudes towards the center of the compartment 250. The protruding ledge 228 is configured to nest within the recess 239.

The second removable seal 255 is sealed against the second compartment 250, with the second compartment 250 and the second removable seal 255 defining a second sealed region. The second removable seal 255 can include a second pull tab 260 for a user to grab in order to remove the second removable seal 255 and access second compartment 250.

The second removable seal 255 can include graphics, symbols, diagrams, words or other instructions to indicate that it is to be opened second. For example, the second removable seal 255 can include the number "2". The second removable portion may also include graphics, symbols, diagrams, words or other instructions to indicate the intended use of the needle stored in the second compartment 250. For example, if the needle stored in the second compartment 250 is to be used for injecting a patient, the second removable seal 255 can include a graphic showing a person with a syringe. Furthermore, if the needle stored in the second compartment 250 is a single-use needle device that locks after use, the second removable seal 255 can also include a lock symbol.

Figure 6:
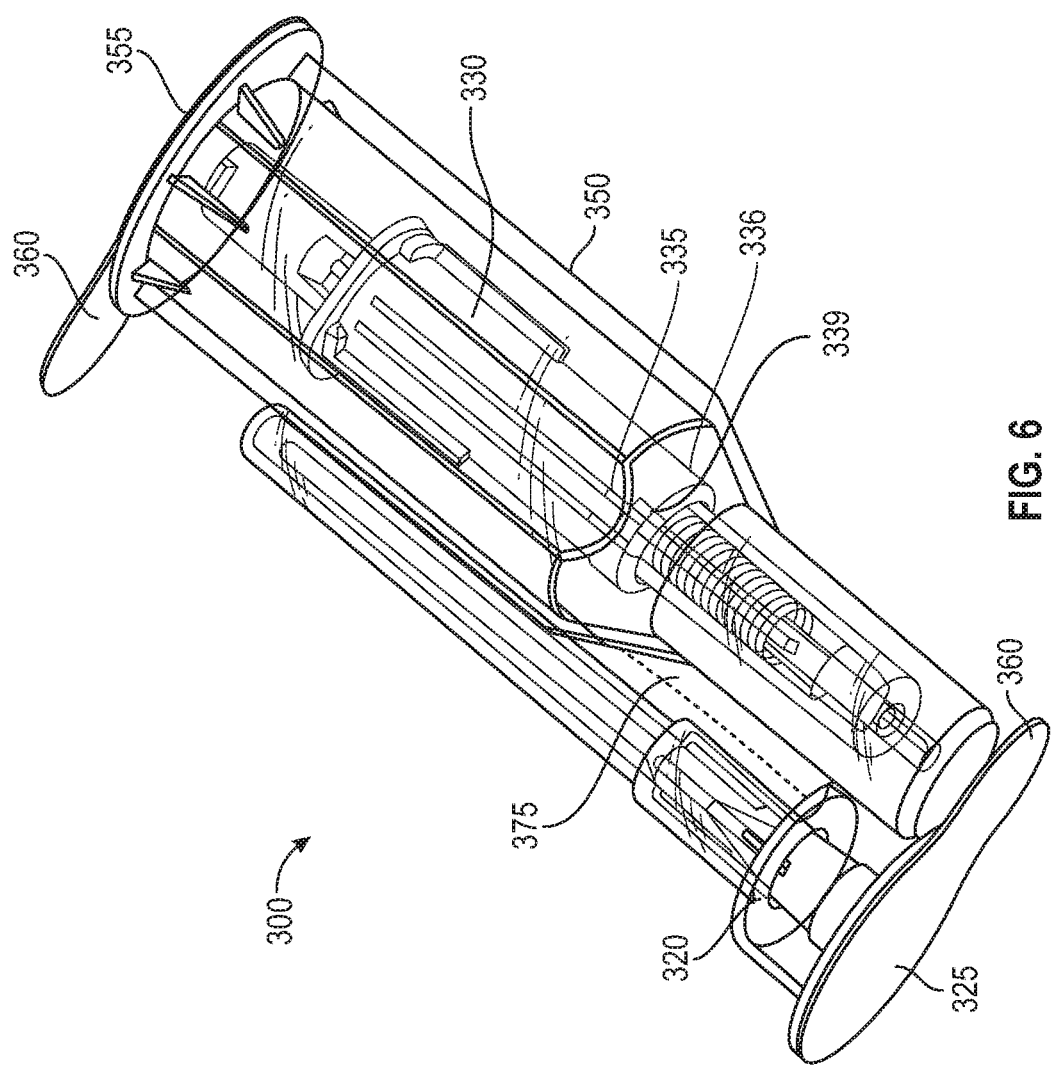
FIG. 6 illustrates a hard package having two removable portions with two pull tab.

FIG. 6 illustrates an exemplary embodiment of a dual packaging system 300. The packing system has a first compartment 320 that can house a first needle and a second compartment 350 that can house a safety needle device 330. As shown in in FIG. 4, the first compartment 320 and second compartment 350 can be molded separately and joined by an attachment 375. In one or more embodiments, the first compartment 320 can be attached to the second compartment 350 via press fitting, an adhesive bond, a solvent bond, a ring connector, a snap fit, a C-clip snap, heat staking or ultrasonic welding. In one or more embodiments, the first compartment 320 can be attached to the second compartment 350 by a perforated or temporary attachment.

In one or more embodiments, the first compartment 320 and the second compartment 350 are composed of different materials or have different colors. For example, in one or more embodiments the first compartment 320 can be colored to indicate a specific use (e.g. red to indicate a blunt fill needle) and the second compartment 350 can be clear, semi-transparent or have a different color indicating a specific use. In other embodiments, both the first compartment 320 and the second compartment 350 are clear or semi-transparent, or are the same color.

The first compartment 320 has an opening that is covered by a removable portion 325. The first removable seal 325 is sealed against the first compartment 320, with the first compartment 320 and the first removable seal 325 defining a first sealed region. The first removable seal 325 can include a first pull tab for a user to grab in order to remove the first removable seal 325 to access the first compartment 320.

The second compartment 350 has an opening that is covered by a second removable seal 355. The second removable seal 355 is sealed against the second compartment 350, with the second compartment 350 and the second removable seal 355 defining a second sealed region. The second removable seal 355 can include a second pull tab 360 for a user to grab in order to remove the second removable seal 355 and access the second compartment 350.

Second compartment 350 includes a premature activation prevention element 335 in the compartment which nests within a recess 339 of a tether 336 of the safety needle device 330. In one or more embodiments, the premature activation prevention element 335 interdigitates with the recess 339 of the tether 336 of the safety needle device 330. The second removable seal 355 is sealed against the second compartment 350, with the second compartment 350 and the second removable seal 355 defining a second sealed region. The second removable seal 355 can include a second pull tab 360 for a user to grab in order to remove the second removable seal 355 and access second compartment 350.

The first removable seal 325 and second removable seal 355 can include any of the features described above for the first removable seal 325 and second removable seal 355, such as graphics, symbols, diagrams, words or other instructions to indicate the order of opening compartments or the intended use of the needles stored in the compartments.

Figure 7:
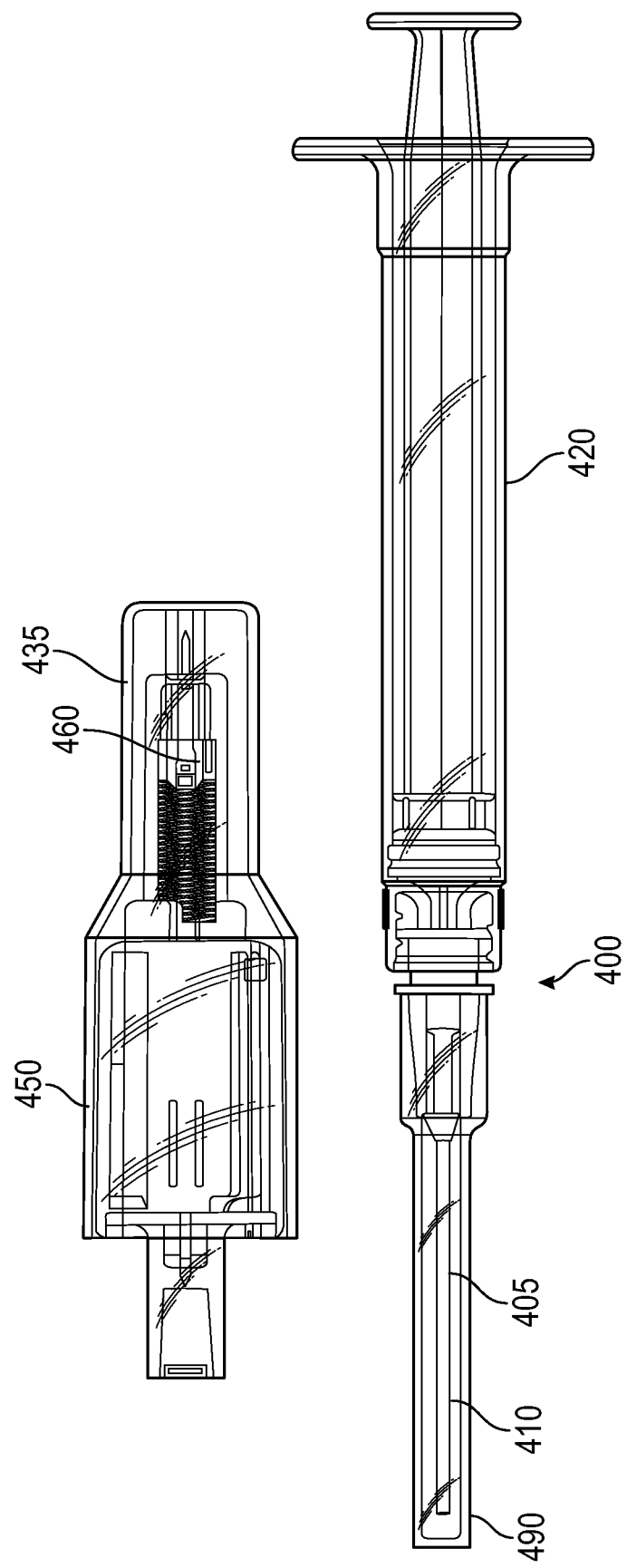
FIG. 7 illustrates a blister pack containing a blunt fill needle and a safety needle.

One or more embodiments of the present disclosure relate to a dual packaging system having a blister package. An exemplary embodiment of a dual packaging system 400 is shown in FIG. 7. A first cavity 420 houses at least a portion of a needle 405, and a second cavity 450 houses at least a portion of a safety needle device 435. In one or more embodiments, first cavity 420 houses a syringe and pre-attached blunt fill needle. Safety needle device 435 having a protruding activation element 436. In one or more embodiments, needle 405 and safety needle device 435 can be packed side by side in dual blister packaging system 400.

In one or more embodiments, second cavity 450 having a recess 460 to nest the protruding activation element of the safety needle device. The distal portion 410 of the needle 405 can be covered with a more rigid material than the proximal portion 415 of the first needle. The distal portion 410 of the needle 405 can be covered by a cap 490. Similarly, the distal portion 440 of the safety needle device 435 can be covered with a rigid material. The distal portion 445 of the safety needle device 435 can be covered by a cap 490. A backing 485 can provide a seal against the first cavity 420 and the second cavity 450. The blister package can also include a peel tab 495 to open the blister package. In one or more embodiments, direction of peel is on the right hand side of the packaging to reduce the chance of contamination. In another embodiment, direction of peel is on the left hand side of the packaging.

Reference throughout this specification to "one embodiment," "certain embodiments," "various embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in various embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein provided a description with reference to particular embodiments, it is to be understood that these embodiments are merely illustrative of the principles and applications of the disclosure. It will be apparent to those skilled in the art that various modifications and variations can be made to the present disclosure without departing from the spirit and scope thereof. Thus, it is intended that the present disclosure include modifications and variations that are within the scope of the appended claims and their equivalents.

What is claimed is:

1. A packaging system comprising:
a safety needle device having a tether and a retractable sleeve, the tether including a recess disposed on a distal end of the tether; and
a hard package having a closed distal end, an open proximal end, and a compartment extending between the closed distal end and the open proximal end;
a premature activation prevention element of the compartment to nest within the recess of the safety needle device; and
a removable seal disposed against the open proximal end, the compartment and the removable seal defining a sealed region, the safety needle device being disposed within the sealed region.

2. The packaging system of claim 1, wherein the safety needle device is a passive safety needle or an active safety needle.

3. The packaging system of claim 1, wherein the premature activation prevention element comprises at least one rail, the at least one rail having a protruding ledge extending from an inner sidewall of the compartment, the protruding ledge extending toward the center of the compartment.

4. The packaging system of claim 3, wherein the protruding ledge has a width that is slightly less than the width of the recess of the safety needle device, the protruding ledge preventing rotation of the safety needle device when the safety needle device is disposed within the compartment.

5. A packaging system comprising:
a safety needle device having a housing, a tether and a retractable sleeve, the retractable sleeve advanceable within the tether, the tether having a recess disposed on a distal end of the tether;
a first hard package comprising a first compartment;
a second hard package having a closed distal end, an open proximal end, and a second compartment extending between the closed distal end and the open proximal end;
a premature activation prevention element disposed on an inner sidewall of the compartment to removably nest within the recess of the tether of the safety needle device, the premature activation prevention element being at least one rail, the at least one rail having a protruding ledge which nests within the recess of the safety needle device;
a first removable seal sealed against the first compartment, the first compartment and the first removable seal defining a first sealed region, the needle being disposed within the first sealed region;
a second removable seal sealed against the second compartment, the second compartment, the second removable seal defining a second sealed region, the safety needle device being disposed within the second sealed region wherein the first hard package is attached to the second hard package.

6. The packaging system of claim 5, wherein the least one rail disposed on an inner sidewall of the compartment extends from a closed distal end of the compartment at least partially the length of the compartment.

7. The packaging system of claim 6, wherein the least one rail disposed on an inner sidewall of the compartment extends from a closed distal end of the compartment to the open proximal end.

8. The packaging system of claim 5, wherein the least one rail has a width that is less than a width of the recess of the safety needle device.

9. The packaging system of claim 5, wherein the first hard package is attached to the second hard package via press fitting, an adhesive bond, a solvent bond, a ring connector, a snap fit, a C-clip snap, heat staking or ultrasonic welding.

10. The packaging system of claim 5, wherein the first hard package has a perforated attachment to the second hard package.

11. The packaging system of claim 5, wherein the first removable portion comprises a first pull tab and the second removable portion comprises a second pull tab.

12. The packaging system of claim 11, wherein the first removable seal includes graphics, symbols, diagrams, words or instructions to indicate that the first removable seal is to be opened first.

13. The packaging system of claim 11, wherein the second removable seal includes graphics, symbols, diagrams, words or instructions to indicate that the first removable seal is to be opened second.

14. The packaging system of claim 11, wherein the first hard package has a first color and the second hard package has a second color.

15. A packaging system comprising:
a needle having a distal end and a proximal end;
a safety needle device having a recess disposed on a distal end of the tether; and
a blister package having a first cavity and a second cavity having a premature activation prevention element to nest within the recess of the safety needle device, the first and second cavities sealed against a backing, the first cavity and the backing defining a first sealed region, the second cavity and the backing defining a second sealed region, the distal end of the needle being disposed within the first sealed region and the distal end of a second needle being disposed within the second sealed region.

16. The packaging system of claim 15, wherein the needle is a blunt fill needle.

17. The packaging system of claim 15, wherein the safety needle device is a passive safety needle or an active safety needle.

18. The packaging system of claim 15, wherein the recess has a width that is slightly larger than a width of the protruding activation element of the compartment, the protruding activation element preventing rotation of the safety needle device when the protruding activation element is nested within the recess.

19. The packaging system of claim 15, further comprising a cap disposed about the distal end of the needle.

20. The packaging system of claim 15, wherein the blister package includes a peel tab.

* * * * *